United States Patent
Montes De Oca Balderas et al.

(10) Patent No.: US 9,770,534 B2
(45) Date of Patent: Sep. 26, 2017

(54) GRAFT FIXATION

(75) Inventors: Horacio Montes De Oca Balderas, York (GB); Malcolm Brown, Otley (GB); Graeme Howling, Leeds (GB); Steve Fenwick, York (GB); Nicholas Cotton, Westborough, MA (US); David Brumfield, Collierville, TN (US)

(73) Assignee: Smith & Nephew, Inc., Memphis, TN (US)

(*) Notice: Subject to any disclaimer, the term of this patent is extended or adjusted under 35 U.S.C. 154(b) by 495 days.

(21) Appl. No.: 12/595,114

(22) PCT Filed: Apr. 16, 2008

(86) PCT No.: PCT/US2008/060401
§ 371 (c)(1),
(2), (4) Date: Oct. 8, 2009

(87) PCT Pub. No.: WO2008/130954
PCT Pub. Date: Oct. 30, 2008

(65) Prior Publication Data
US 2010/0145448 A1    Jun. 10, 2010

Related U.S. Application Data

(60) Provisional application No. 60/912,828, filed on Apr. 19, 2007.

(51) Int. Cl.
*A61F 2/08* (2006.01)
*A61L 27/50* (2006.01)
(Continued)

(52) U.S. Cl.
CPC ............. *A61L 27/50* (2013.01); *A61F 2/0811* (2013.01); *A61L 27/14* (2013.01);
(Continued)

(58) Field of Classification Search
CPC ........................................................ A61F 2/08
(Continued)

(56) References Cited

U.S. PATENT DOCUMENTS 3,531,561 A    9/1970    Trehu
3,636,956 A    1/1972    Schneider
(Continued)

FOREIGN PATENT DOCUMENTS

AU    2008240418        4/2008
AU    2008240418 A1    10/2008
(Continued)

OTHER PUBLICATIONS

International Search Report and Written Opinion for PCT/US2008/060401 Dated Jan. 9, 2009.
(Continued)

*Primary Examiner* — Yashita Sharma
(74) *Attorney, Agent, or Firm* — Burns & Levinson LLP; Joseph M. Maraia (57) ABSTRACT

The present disclosure relates to an anchor for fixating a tissue graft to bone. The anchor includes a through hole extending an entire length of the anchor and a polymer composition having shape memory qualities. Other anchors and methods for fixating a tissue graft to bone are also disclosed.

4 Claims, 8 Drawing Sheets

(51) Int. Cl.
*A61L 27/14* (2006.01)
*A61B 17/00* (2006.01)

(52) U.S. Cl.
CPC .............. *A61B 2017/00004* (2013.01); *A61B 2017/00871* (2013.01); *A61F 2002/0852* (2013.01); *A61F 2002/0858* (2013.01); *A61F 2002/0864* (2013.01); *A61F 2002/0888* (2013.01); *A61F 2210/0014* (2013.01); *A61L 2400/16* (2013.01)

(58) Field of Classification Search
USPC ........... 623/13.11, 13.14, 13.2, 23.61, 23.62; 606/232, 286, 300–305, 308; 604/399
See application file for complete search history.

(56) References Cited

U.S. PATENT DOCUMENTS

| | | |
|---|---|---|
| 3,736,646 A | 6/1973 | Schmitt et al. |
| 3,797,499 A | 3/1974 | Schneider |
| 3,856,905 A | 12/1974 | Dawson |
| 3,926,459 A | 12/1975 | Pontigny |
| 4,137,921 A | 2/1979 | Okuzumi et al. |
| 4,181,983 A | 1/1980 | Kulkarni |
| 4,438,253 A | 3/1984 | Casey et al. |
| 4,523,591 A | 6/1985 | Kaplan et al. |
| 4,539,981 A | 9/1985 | Tunc |
| 4,559,945 A | 12/1985 | Koelmel et al. |
| 4,636,215 A | 1/1987 | Schwartz |
| 4,700,704 A | 10/1987 | Jamiolkowski et al. |
| 4,756,307 A | 7/1988 | Crowninshield |
| 4,916,207 A | 4/1990 | Boyle, Jr. et al. |
| 4,938,763 A | 7/1990 | Dunn et al. |
| 4,950,258 A | 8/1990 | Kawai et al. |
| 4,968,317 A | 11/1990 | Tormala et al. |
| 4,990,161 A | 2/1991 | Kampner |
| 5,049,591 A | 9/1991 | Hayashi et al. |
| 5,053,035 A | 10/1991 | Mclaren |
| 5,061,181 A | 10/1991 | Niznick |
| 5,108,289 A | 4/1992 | Fukuyo |
| 5,108,755 A | 4/1992 | Daniels et al. |
| 5,110,852 A | 5/1992 | Gogolewski et al. |
| 5,192,301 A | 3/1993 | Kamiya et al. |
| 5,201,771 A | 4/1993 | Belykh et al. |
| 5,208,305 A | 5/1993 | Grootaert |
| 5,250,584 A | 10/1993 | Ikada et al. |
| 5,266,608 A | 11/1993 | Katz et al. |
| 5,275,601 A | 1/1994 | Gogolewski et al. |
| 5,294,395 A | 3/1994 | Broyer |
| 5,324,308 A | 6/1994 | Pierce |
| 5,333,624 A | 8/1994 | Tovey |
| 5,360,448 A | 11/1994 | Thramann |
| 5,364,400 A | 11/1994 | Rego, Jr. et al. |
| 5,376,120 A | 12/1994 | Sarver et al. |
| 5,383,931 A | 1/1995 | Hehli et al. |
| 5,407,445 A | 4/1995 | Tautvydas et al. |
| 5,417,712 A * | 5/1995 | Whittaker et al. ............ 606/232 |
| 5,437,918 A | 8/1995 | Taniguchi et al. |
| 5,441,515 A | 8/1995 | Khosravi et al. |
| 5,458,653 A | 10/1995 | Davidson |
| 5,470,334 A | 11/1995 | Ross et al. |
| 5,525,706 A | 6/1996 | Gruber et al. |
| 5,527,337 A | 6/1996 | Stack et al. |
| 5,527,341 A | 6/1996 | Gogolewski et al. |
| 5,562,704 A | 10/1996 | Tamminmaki et al. |
| 5,567,431 A | 10/1996 | Vert et al. |
| 5,569,250 A | 10/1996 | Sarver et al. |
| 5,571,193 A | 11/1996 | Kampner |
| 5,571,204 A | 11/1996 | Nies |
| 5,633,002 A | 5/1997 | Stricker et al. |
| 5,634,936 A | 6/1997 | Linden et al. |
| 5,641,502 A | 6/1997 | Skalla et al. |
| 5,660,846 A | 8/1997 | Cheikh |
| 5,665,831 A | 9/1997 | Neuenschwander et al. |
| 5,670,161 A | 9/1997 | Healy et al. |
| 5,676,699 A | 10/1997 | Gogolewski et al. |
| 5,690,671 A | 11/1997 | McGurk et al. |
| 5,695,497 A | 12/1997 | Stahelin |
| 5,700,901 A | 12/1997 | Hurst et al. |
| 5,716,410 A | 2/1998 | Wang et al. |
| 5,716,413 A | 2/1998 | Walter et al. |
| 5,733,330 A | 3/1998 | Cox |
| 5,741,329 A | 4/1998 | Agrawal et al. |
| 5,760,118 A | 6/1998 | Sinclair et al. |
| 5,766,239 A | 6/1998 | Cox |
| 5,766,618 A | 6/1998 | Laurencin et al. |
| 5,792,400 A | 8/1998 | Talja et al. |
| 5,817,328 A | 10/1998 | Gresser et al. |
| 5,834,582 A | 11/1998 | Sinclair et al. |
| 5,837,276 A | 11/1998 | Cheikh |
| 5,853,639 A | 12/1998 | Kawakami et al. |
| 5,863,297 A | 1/1999 | Walter et al. |
| 5,868,746 A | 2/1999 | Sarver et al. |
| 5,893,850 A | 4/1999 | Cachia |
| 5,902,599 A | 5/1999 | Anseth et al. |
| 5,904,658 A | 5/1999 | Niederauer et al. |
| 5,908,918 A | 6/1999 | Chen et al. |
| 5,935,172 A | 8/1999 | Ochoa et al. |
| 5,939,453 A | 8/1999 | Heiler et al. |
| 5,947,893 A | 9/1999 | Agrawal et al. |
| 5,951,288 A | 9/1999 | Sawa |
| 5,968,092 A | 10/1999 | Buscemi et al. |
| 5,977,204 A | 11/1999 | Boyan et al. |
| 5,980,564 A | 11/1999 | Stinson |
| 5,997,580 A | 12/1999 | Mastrorio et al. |
| 5,997,582 A | 12/1999 | Weiss |
| 6,001,100 A | 12/1999 | Sherman et al. |
| 6,001,101 A | 12/1999 | Augagneur et al. |
| 6,005,161 A | 12/1999 | Brekke et al. |
| 6,071,982 A | 6/2000 | Wise et al. |
| 6,077,989 A | 6/2000 | Kandel et al. |
| 6,113,624 A | 9/2000 | Bezwada et al. |
| 6,136,369 A | 10/2000 | Leitao et al. |
| 6,150,497 A | 11/2000 | Sastry et al. |
| 6,156,842 A | 12/2000 | Hoenig et al. |
| 6,160,084 A | 12/2000 | Langer et al. |
| 6,162,225 A | 12/2000 | Gertzman et al. |
| 6,168,570 B1 | 1/2001 | Ferrera |
| 6,179,842 B1 | 1/2001 | Spotorno et al. |
| 6,203,573 B1 | 3/2001 | Walter et al. |
| 6,206,883 B1 | 3/2001 | Tunc |
| 6,248,108 B1 | 6/2001 | Tormala et al. |
| 6,248,430 B1 | 6/2001 | Toyoda et al. |
| 6,277,390 B1 | 8/2001 | Schaffner |
| 6,281,262 B1 | 8/2001 | Shikinami |
| 6,283,973 B1 | 9/2001 | Hubbard et al. |
| 6,293,950 B1 | 9/2001 | Lynch et al. |
| 6,299,448 B1 | 10/2001 | Zdrahala et al. |
| 6,303,697 B1 | 10/2001 | Yuan et al. |
| 6,315,788 B1 | 11/2001 | Roby |
| 6,344,496 B1 | 2/2002 | Niederauer et al. |
| 6,375,465 B1 | 4/2002 | Engman et al. |
| 6,388,043 B1 | 5/2002 | Langer et al. |
| 6,406,498 B1 | 6/2002 | Tormala et al. |
| 6,425,923 B1 | 7/2002 | Stalcup et al. |
| 6,436,136 B1 | 8/2002 | Flodin et al. |
| 6,447,515 B1 | 9/2002 | Meldrum |
| 6,468,277 B1 | 10/2002 | Justin et al. |
| 6,486,296 B1 | 11/2002 | Shimamoto et al. |
| 6,488,938 B1 | 12/2002 | Ogura et al. |
| 6,503,278 B1 | 1/2003 | Pohjonen et al. |
| 6,508,830 B2 * | 1/2003 | Steiner .......................... 606/232 |
| 6,511,511 B1 | 1/2003 | Slivka et al. |
| 6,514,286 B1 | 2/2003 | Leatherbury et al. |
| 6,547,792 B1 | 4/2003 | Tsuji et al. |
| 6,565,606 B1 | 5/2003 | Bruce et al. |
| 6,579,533 B1 | 6/2003 | Tormala et al. |
| 6,583,232 B1 | 6/2003 | Brown |
| 6,599,323 B2 | 7/2003 | Meliean et al. |
| 6,605,090 B1 | 8/2003 | Trieu et al. |
| 6,613,089 B1 | 9/2003 | Estes et al. |
| 6,623,487 B1 | 9/2003 | Goshert |
| 6,652,582 B1 | 11/2003 | Stinson |
| 6,716,957 B2 | 4/2004 | Tunc |

(56) References Cited

U.S. PATENT DOCUMENTS

| | | |
|---|---|---|
| 6,719,935 B2 | 4/2004 | Tunc |
| 6,720,402 B2 | 4/2004 | Langer et al. |
| 6,726,696 B1 | 4/2004 | Houser et al. |
| 6,758,862 B2 | 7/2004 | Berry et al. |
| 6,758,863 B2 | 7/2004 | Estes et al. |
| 6,783,712 B2 | 8/2004 | Slivka et al. |
| 6,827,743 B2 | 12/2004 | Eisermann et al. |
| 6,830,575 B2 | 12/2004 | Stenzel et al. |
| 6,841,111 B2 | 1/2005 | Rickner et al. |
| 6,843,799 B2 | 1/2005 | Bartlett |
| 6,852,825 B2 | 2/2005 | Lendlein et al. |
| 6,869,445 B1 | 3/2005 | Johnson |
| 6,881,766 B2 | 4/2005 | Hain |
| 6,902,584 B2 | 6/2005 | Kwan et al. |
| 6,908,466 B1 | 6/2005 | Bonutti et al. |
| 6,908,624 B2 | 6/2005 | Hossainy et al. |
| 6,916,321 B2 | 7/2005 | TenHuisen et al. |
| 6,951,956 B2 | 10/2005 | Yamane et al. |
| 6,974,862 B2 | 12/2005 | Ringeisen et al. |
| 7,012,106 B2 | 3/2006 | Yuan et al. |
| 7,033,603 B2 | 4/2006 | Nelson et al. |
| 7,192,443 B2 | 3/2007 | Solem et al. |
| 7,208,550 B2 | 4/2007 | Mather et al. |
| 7,214,765 B2 | 5/2007 | Ringeisen et al. |
| 7,261,716 B2 | 8/2007 | Strobel et al. |
| 7,261,734 B2 | 8/2007 | Gellman et al. |
| 7,268,205 B2 | 9/2007 | Williams et al. |
| 7,270,813 B2 | 9/2007 | Shimp et al. |
| 7,285,087 B2 | 10/2007 | Moaddeb et al. |
| 7,285,130 B2 | 10/2007 | Austin |
| 7,314,480 B2 | 1/2008 | Eidenschink et al. |
| 7,335,375 B2 | 2/2008 | Li et al. |
| 7,378,144 B2 | 5/2008 | DeMeo et al. |
| 7,455,674 B2 | 11/2008 | Rose |
| 7,524,891 B2 | 4/2009 | Rose |
| 7,553,923 B2 | 6/2009 | Williams et al. |
| 8,501,215 B2 | 8/2013 | Chen et al. |
| 2001/0012940 A1 | 8/2001 | Tunc |
| 2001/0018614 A1 | 8/2001 | Bianchi |
| 2002/0022588 A1 | 2/2002 | Wilkie et al. |
| 2002/0029041 A1 | 3/2002 | Hover et al. |
| 2002/0029043 A1 | 3/2002 | Ahrens et al. |
| 2002/0071822 A1 | 6/2002 | Uhrich |
| 2002/0082362 A1 | 6/2002 | Broccini et al. |
| 2002/0120348 A1 | 8/2002 | Melican et al. |
| 2002/0138154 A1 | 9/2002 | Li et al. |
| 2002/0143403 A1 | 10/2002 | Vaidyanathan et al. |
| 2002/0150775 A1 | 10/2002 | Ishikawa et al. |
| 2002/0160032 A1 | 10/2002 | Long et al. |
| 2003/0045941 A1 | 3/2003 | Lewallen |
| 2003/0055198 A1 | 3/2003 | Langer et al. |
| 2003/0104031 A1 | 6/2003 | Dumont et al. |
| 2003/0114937 A1 | 6/2003 | Leatherbury et al. |
| 2003/0120280 A1 | 6/2003 | Rolier et al. |
| 2003/0125745 A1 | 7/2003 | Tseng et al. |
| 2003/0130742 A1 | 7/2003 | Connelly et al. |
| 2003/0153971 A1 | 8/2003 | Chandrasekaran |
| 2003/0153972 A1 | 8/2003 | Helmus |
| 2003/0180344 A1 | 9/2003 | Wise et al. |
| 2003/0236573 A1 | 12/2003 | Evans et al. |
| 2004/0002770 A1 | 1/2004 | King et al. |
| 2004/0015187 A1 | 1/2004 | Lendlein et al. |
| 2004/0019386 A1 | 1/2004 | Ferree |
| 2004/0030341 A1 | 2/2004 | Aeschlimann et al. |
| 2004/0030342 A1 | 2/2004 | Trieu et al. |
| 2004/0052992 A1 | 3/2004 | Boone et al. |
| 2004/0054372 A1 | 3/2004 | Corden et al. |
| 2004/0106734 A1 | 6/2004 | Rose |
| 2004/0109823 A1 | 6/2004 | Kaplan |
| 2004/0110285 A1 | 6/2004 | Lendlein et al. |
| 2004/0115239 A1 | 6/2004 | Shastri et al. |
| 2004/0131681 A1 | 7/2004 | Ambrose et al. |
| 2004/0143221 A1 | 7/2004 | Shadduck |
| 2004/0153075 A1 | 8/2004 | Roger |
| 2004/0156878 A1 | 8/2004 | Rezania et al. |
| 2004/0172118 A1 | 9/2004 | Gibson |
| 2004/0193154 A1 | 9/2004 | Leatherbury et al. |
| 2004/0241203 A1 | 12/2004 | Shakesheff et al. |
| 2004/0242722 A1 | 12/2004 | Rose |
| 2004/0254639 A1 | 12/2004 | Li et al. |
| 2004/0258732 A1 | 12/2004 | Shikinami |
| 2004/0259972 A1 | 12/2004 | Ringeisen et al. |
| 2004/0260398 A1 | 12/2004 | Kelman |
| 2004/0265385 A1 | 12/2004 | West |
| 2004/0267263 A1 | 12/2004 | May |
| 2005/0008672 A1 | 1/2005 | Winterbottom et al. |
| 2005/0013793 A1 | 1/2005 | Beckman et al. |
| 2005/0019404 A1 | 1/2005 | Sung et al. |
| 2005/0033295 A1 | 2/2005 | Wisnewski |
| 2005/0043751 A1 | 2/2005 | Phan et al. |
| 2005/0043752 A1 | 2/2005 | Phan et al. |
| 2005/0070928 A1 | 3/2005 | Heino et al. |
| 2005/0080483 A1 | 4/2005 | Solem et al. |
| 2005/0080489 A1 | 4/2005 | Estes et al. |
| 2005/0085313 A1 | 4/2005 | Nishitani |
| 2005/0085812 A1 | 4/2005 | Sherman et al. |
| 2005/0090861 A1 | 4/2005 | Porter |
| 2005/0107886 A1 | 5/2005 | Crabtree et al. |
| 2005/0123582 A1 | 6/2005 | Sung et al. |
| 2005/0125051 A1 | 6/2005 | Eidenschink et al. |
| 2005/0136764 A1 | 6/2005 | Sherman et al. |
| 2005/0137611 A1 | 6/2005 | Escudero et al. |
| 2005/0137715 A1 | 6/2005 | Phan et al. |
| 2005/0159812 A1 | 7/2005 | Dinger, III et al. |
| 2005/0165128 A1 | 7/2005 | Cohn et al. |
| 2005/0177144 A1 | 8/2005 | Phan et al. |
| 2005/0177245 A1 | 8/2005 | Leatherbury et al. |
| 2005/0182411 A1 | 8/2005 | DeMeo et al. |
| 2005/0182428 A1 | 8/2005 | Bearinger et al. |
| 2005/0187602 A1 | 8/2005 | Eidenschink |
| 2005/0196420 A1 | 9/2005 | Zucherman et al. |
| 2005/0197422 A1 | 9/2005 | Mayadunne et al. |
| 2005/0208094 A1 | 9/2005 | Armitage et al. |
| 2005/0209705 A1 | 9/2005 | Niederauer et al. |
| 2005/0240281 A1 | 10/2005 | Slivka et al. |
| 2005/0273106 A1 | 12/2005 | Oepen |
| 2006/0051394 A1 | 3/2006 | Moore et al. |
| 2006/0067973 A1 | 3/2006 | Schachter |
| 2006/0095138 A1 | 5/2006 | Truckai et al. |
| 2006/0121084 A1 | 6/2006 | Borden et al. |
| 2006/0121087 A1 | 6/2006 | Williams et al. |
| 2006/0136071 A1 | 6/2006 | Maspero et al. |
| 2006/0149248 A1 | 7/2006 | Schlienger et al. |
| 2006/0177480 A1 | 8/2006 | Sung et al. |
| 2006/0178739 A1 | 8/2006 | Shalaby et al. |
| 2006/0178748 A1 | 8/2006 | Dinger, III et al. |
| 2006/0188546 A1 | 8/2006 | Giroux |
| 2006/0188547 A1 | 8/2006 | Bezwada |
| 2006/0200150 A1 | 9/2006 | Iiomaki et al. |
| 2006/0207612 A1 | 9/2006 | Jackson et al. |
| 2006/0247610 A1 | 11/2006 | Lanphere et al. |
| 2006/0263335 A1 | 11/2006 | France et al. |
| 2006/0264948 A1 | 11/2006 | Williams |
| 2006/0293749 A1 | 12/2006 | Hudgins et al. |
| 2007/0005094 A1 | 1/2007 | Eaton et al. |
| 2007/0014831 A1 | 1/2007 | Sung et al. |
| 2007/0041950 A1 | 2/2007 | Leatherbury et al. |
| 2007/0043376 A1 | 2/2007 | Leatherbury et al. |
| 2007/0043433 A1 | 2/2007 | Chandrasekaran |
| 2007/0048383 A1 | 3/2007 | Helmus |
| 2007/0050018 A1 | 3/2007 | Wainwright |
| 2007/0065652 A1 | 3/2007 | Liebschner |
| 2007/0067043 A1 | 3/2007 | Dericks |
| 2007/0083205 A1 | 4/2007 | Attawia et al. |
| 2007/0100449 A1 | 5/2007 | O'Neil et al. |
| 2007/0128154 A1 | 6/2007 | Hadba et al. |
| 2007/0134305 A1 | 6/2007 | Zilberman |
| 2007/0141111 A1 | 6/2007 | Suokas et al. |
| 2007/0156251 A1 | 7/2007 | Karmon |
| 2007/0162019 A1 | 7/2007 | Burns et al. |
| 2007/0182041 A1 | 8/2007 | Rizk et al. |
| 2007/0191963 A1 | 8/2007 | Winterbottom et al. |
| 2007/0213828 A1 | 9/2007 | Trieu et al. |
| 2007/0260324 A1 | 11/2007 | Joshi et al. |

(56) References Cited

U.S. PATENT DOCUMENTS

| | | |
|---|---|---|
| 2007/0265622 A1 | 11/2007 | Aeschlimann et al. |
| 2007/0270852 A1 | 11/2007 | Tormala et al. |
| 2007/0276366 A1 | 11/2007 | Gaines, Jr. |
| 2007/0280983 A1 | 12/2007 | Strickler et al. |
| 2007/0299151 A1 | 12/2007 | Guelcher et al. |
| 2007/0299156 A1 | 12/2007 | Brown |
| 2007/0299449 A1 | 12/2007 | Allinniemi et al. |
| 2008/0015578 A1 | 1/2008 | Erickson et al. |
| 2008/0077140 A1 | 3/2008 | Osman |
| 2008/0085297 A1 | 4/2008 | Dave et al. |
| 2008/0086199 A1 | 4/2008 | Dave et al. |
| 2008/0109037 A1* | 5/2008 | Steiner et al. .............. 606/232 |
| 2008/0154368 A1 | 6/2008 | Justis et al. |
| 2008/0154373 A1 | 6/2008 | Protopsaltis et al. |
| 2008/0200638 A1 | 8/2008 | Redepenning |
| 2008/0206297 A1 | 8/2008 | Roeder et al. |
| 2008/0228186 A1* | 9/2008 | Gall et al. .................... 606/63 |
| 2008/0234754 A1 | 9/2008 | McCarthy et al. |
| 2008/0234762 A1 | 9/2008 | Forstein et al. |
| 2008/0241211 A1 | 10/2008 | Han et al. |
| 2008/0249633 A1 | 10/2008 | Wu |
| 2008/0262613 A1 | 10/2008 | Gogolewski |
| 2008/0305144 A1 | 12/2008 | Brown et al. |
| 2009/0030160 A1 | 1/2009 | Kanazawa |
| 2009/0048145 A1 | 2/2009 | Hellerbrand et al. |
| 2009/0093888 A1 | 4/2009 | Dawson et al. |
| 2009/0099600 A1 | 4/2009 | Moore et al. |
| 2009/0149856 A1 | 6/2009 | Paakinaho et al. |
| 2009/0171064 A1 | 7/2009 | Arimura et al. |
| 2009/0204116 A1 | 8/2009 | Shalaby et al. |
| 2009/0270923 A1 | 10/2009 | Tormala et al. |
| 2009/0274742 A1 | 11/2009 | Brown |
| 2010/0136648 A1 | 6/2010 | Balderas et al. |

FOREIGN PATENT DOCUMENTS

| | | |
|---|---|---|
| CA | 2254002 | 5/2000 |
| CN | 1857742 | 11/2006 |
| DE | 1604403 B1 | 11/1970 |
| DE | 2817778 | 11/1978 |
| DE | 2947985 | 9/1981 |
| DE | 3036611 A1 | 6/1982 |
| DE | 3936188 | 5/1990 |
| DE | 4226465 | 2/1993 |
| DE | 4220216 | 1/1994 |
| DE | 102005032005 A1 | 1/2007 |
| EP | 204931 | 12/1986 |
| EP | 299004 | 1/1989 |
| EP | 321389 | 6/1989 |
| EP | 326426 | 8/1989 |
| EP | 401844 | 12/1990 |
| EP | 404004 | 12/1990 |
| EP | 439892 | 8/1991 |
| EP | 475077 | 3/1992 |
| EP | 590656 | 4/1994 |
| EP | 595956 | 5/1994 |
| EP | 326426 B1 | 12/1994 |
| EP | 635274 | 1/1995 |
| EP | 531487 | 1/1996 |
| EP | 711534 | 5/1996 |
| EP | 747072 | 12/1996 |
| EP | 751165 | 1/1997 |
| EP | 803521 | 10/1997 |
| EP | 805175 | 11/1997 |
| EP | 806283 | 11/1997 |
| EP | 1000958 A1 | 5/2000 |
| EP | 1009448 | 6/2000 |
| EP | 1056487 | 12/2000 |
| EP | 1086711 | 3/2001 |
| EP | 1136510 | 9/2001 |
| EP | 1142597 | 10/2001 |
| EP | 1093774 | 6/2002 |
| EP | 1216717 | 6/2002 |
| EP | 1277482 | 1/2003 |
| EP | 815809 | 3/2004 |
| EP | 1284756 | 9/2004 |
| FR | 2691901 | 10/1993 |
| FR | 2691901 A1 | 12/1993 |
| FR | 2863478 A1 | 6/2005 |
| GB | 807589 | 1/1959 |
| GB | 1416575 A | 12/1975 |
| GB | 2215209 | 9/1989 |
| JP | 62-199429 | 9/1987 |
| JP | 01-192367 | 8/1989 |
| JP | 2169612 | 6/1990 |
| JP | 02-270519 | 11/1990 |
| JP | 03-021613 | 1/1991 |
| JP | 05-147105 | 6/1993 |
| JP | 06-065460 | 3/1994 |
| JP | 06-234157 | 8/1994 |
| JP | 8196617 | 8/1996 |
| JP | 9040761 | 2/1997 |
| JP | 9095606 | 4/1997 |
| JP | 9221539 | 8/1997 |
| JP | 9234241 | 9/1997 |
| JP | 9272790 | 10/1997 |
| JP | 10176039 | 6/1998 |
| JP | 10309313 | 11/1998 |
| JP | 11209595 | 8/1999 |
| JP | 2003-094516 | 4/2003 |
| JP | 2003-518230 | 6/2003 |
| JP | 3503045 | 3/2004 |
| JP | 2006-503172 | 1/2006 |
| JP | 2007046050 | 2/2007 |
| KR | 0180858 | 4/1999 |
| WO | 8404311 | 11/1984 |
| WO | 9003768 | 4/1990 |
| WO | 9301773 | 2/1993 |
| WO | 9534331 | 12/1995 |
| WO | 96/22061 A1 | 7/1996 |
| WO | 9705193 | 2/1997 |
| WO | 9725936 | 7/1997 |
| WO | 97/29673 | 8/1997 |
| WO | 9736555 | 10/1997 |
| WO | 98/00141 A1 | 1/1998 |
| WO | 9826814 | 6/1998 |
| WO | 9830141 | 7/1998 |
| WO | 9847445 | 10/1998 |
| WO | 9911296 | 3/1999 |
| WO | 9911297 | 3/1999 |
| WO | 9922770 | 5/1999 |
| WO | 0001426 | 1/2000 |
| WO | 00/56376 | 9/2000 |
| WO | 00/56376 A1 | 9/2000 |
| WO | 0146501 | 6/2001 |
| WO | 0196105 | 12/2001 |
| WO | 0200137 | 1/2002 |
| WO | 0234159 | 5/2002 |
| WO | 0234310 | 5/2002 |
| WO | 02076725 | 10/2002 |
| WO | 03004071 | 1/2003 |
| WO | 03064531 | 8/2003 |
| WO | 2004011054 | 2/2004 |
| WO | 2004071356 | 8/2004 |
| WO | 2004110313 | 12/2004 |
| WO | 2005014718 | 2/2005 |
| WO | 2005028534 | 3/2005 |
| WO | 2005046470 | 5/2005 |
| WO | 2005085313 | 9/2005 |
| WO | 2005112804 | 12/2005 |
| WO | 2006053936 | 5/2006 |
| WO | 2006064025 | 6/2006 |
| WO | 2006095138 A1 | 9/2006 |
| WO | 2006108114 | 10/2006 |
| WO | 2006114483 | 11/2006 |
| WO | 2006116129 | 1/2007 |
| WO | 2007020430 | 2/2007 |
| WO | 2007020432 | 2/2007 |
| WO | 2007021593 | 2/2007 |
| WO | 2007023296 | 3/2007 |
| WO | 2007024492 | 3/2007 |
| WO | WO2007038009 A2 | 4/2007 |
| WO | 2007065074 | 6/2007 |
| WO | 2007084609 | 7/2007 |

(56) References Cited

FOREIGN PATENT DOCUMENTS

| WO | 2007086832 | 8/2007 |
|---|---|---|
| WO | 2007111808 | 10/2007 |
| WO | 2007117499 | 10/2007 |
| WO | 2008001633 | 1/2008 |
| WO | 2008004011 A1 | 1/2008 |
| WO | 2008116591 | 3/2008 |
| WO | 2008044011 | 4/2008 |
| WO | 2008067531 | 6/2008 |
| WO | 2008067561 A2 | 6/2008 |
| WO | 2008089172 | 7/2008 |
| WO | 2008098019 | 8/2008 |
| WO | 2008101932 | 8/2008 |
| WO | 2008112875 A2 | 9/2008 |
| WO | 2008112880 A2 | 9/2008 |
| WO | 2008112912 | 9/2008 |
| WO | 2008131197 | 10/2008 |
| WO | 2008134264 | 11/2008 |
| WO | 03004071 | 1/2013 |

OTHER PUBLICATIONS

Zegzula, et al., 'Bone Formation with Use of rhBMP-2 (Recombinant Human Bone Morphogenetic Protein-2,' The Journal of Bone and Joint Surgery, 79:1778-1790 (1997).

Zhang, Biodegradable lactide polymers: synthesis, degradation, and controlled drug release properties (drug release), Queen's University at Kingston, Canada, vol. 55/01-B of Dissertation Abstracts International, p. i-xv, 1-179 (Oct. 1993).

English Translation of Japanese Office Action dated Jun. 19, 2012 for JP Application 2010-504182. p. 1-6.

First Office Action for Patent Application No. JP 2010-504201, mail-dated Mar. 19, 2013, 5 pages.

Ofer Nativ, et al., "Bladder Neck Suspension Using Bone Anchors for the Treatment of Female Stress Incontinence," ASAIO Journal, vol. 43 No. 3, pp. 204-208 and cover, May-Jun. 1997, 6 pages.

Mitsura Momma, et al., "Long Bone Intramedullary Fixation Method Using Shape Memory Anchoring Nails—An Attempt at a Biomechanical Test and the Application Thereof to Proximal Humeral Fractures," Journal of the Eastern Japan Association of Orthopaedics and Traumatology, vol. 12, No. 4, pp. 385-390 and back cover, 2000, 8 pages.

Notice of Reasons for Rejection for Japanese Patent Application No. 2010-504201 dated Nov. 26, 2013, 10 pages and English translation thereof.

Andriano, et al., 'Processing and characterization of absorbable polylactide polymers for use in surgical implants,' Journal of Applied Biomaterials, 5(2):133-140 (1994).

Asano, et al., 'In vivo characteristics of low molecular weight copoly(D.L-lactic acid) formulations with controlled release of LH-RH agonist,' Biomaterials, 10(8):569-573 (1989).

Barca, et al., 'Resorbable poly-L-lactic acid mini-staples for the fixation of Akin osteotomies,' The Journal of Foot and Ankle Surgery, 36(2):106-111 (1997).

Bartenev et al.; On the theory of biaxial orientation of amorphous polymers, Mechanics of Composite Materials, 1973, vol. 6, p. 671-677.

Bertrand, et al., Biocompatibility Aspects of New Stent Technology, JACC, 32(3):562-571 (1998).

Celikkaya, et al., 'Poly(DL-lactide)/Poly(ethylene glycol) Copolymer Particles. I. Preparation and Characterization,' Journal of Applied Polymer Science, 61: 1439-1446 (1996).

D. Hull and T. W. Clyne, 'An introduction to composite materials,' Second Edition, Cambridge University Press, Table of Contents, (1996) 8 pages.

D. Wheeler, et al., 'Effect of bioactive glass particle size on osseous regeneration of cancellous defects,' J. Biomed. Materials Research, 41(4):527-533 (1998).

Daniels, et al., 'Mechanical properties of biodegradable polymers and composites proposed for internal fixation of bone,' J. Applied Biomaterials, 1 :57-78 (1990).

Dauner, et al. 'Resorbable continuous-fiber reinforced polymers for osteosynthesis,' J. Materials Science Materials in Medicine, 9: 173-179 (1998).

Eling, et al., 'Biodegradable Materials of Poly(L-Lactic Acid): 1. Melt-Spun and Solution-Spun Fibres,' Polymer, 23:1587-1593 (1982).

Fambri, et al., 'Biodegradable fibres of poly(I-lactic acid) produced by melt spinning,' Polymer, 38:79-85 (1997).

Frenger, 'Biomedical Uses of Shape Memory Polymers,' Biomed. Sci. Instrum., 29:47-50 (1993).

Fukuzaki, et al., Synthesis of copoly(D,L-Lactic acid) with relatively low molecular weight and in vitro degradation, Japan Atomic Energy Research Institute, Gunma, Jpn, European Polymer Journal,25(10):1019-1026 (1989).

Gautier, et al., 'Poly(a-hydroxyacids) for application in the spinal cord: Resorbability and biocompatibility with adult rate Schwann cells and spinal cord,' Journal of Biomedical Materials Research, 42(4):642-654 (1998).

Giardina, et al., 'Experimental evaluation of a resorbable intramedullary plug for cemented total hip replacement,' Biomaterials, 18(13):907-913 (1997).

Gogolewsji, et al., 'Resorbable materials of poly(L-lactide). II Fibers spun from solutions of poly(L-lactide) in good solvents,' J. Appl. Polymer Sci., 28:1045-1061 (1983).

Grijpma et al., 'Chain Entanglement Mechanical Properties and Drawability of Poly (Lactide),' Colloid Polym Sci., 272:1068-1081 (1994).

Haers, et al., 'Biodegradable polyactide plates and screws in orthognathic surgery,' Technical Note, Journal of Cranio-Maxillofacial Surgery, 26(2):87-91 (1998).

Hyon, et al., 'Effects of residual monomer on the degradation of DL-lactide polymer,' Hyon, Jamshidi & Ikada, Polymer International, 46:196-202 (1998).

J. West et al, 'Bioactive Polymers, Synthetic biodegradable polymer scaffolds,' Chapter 5, pp. 83-95, Anthony Atala and David J. Mooney, Editors; Joseph P. Vacanti and Robert Langer, Associate Editors, Birkhauser (1997).

Kaitian, et al., 'Poly(D,L-Lactic Acid) Homopolymers: Synthesis and Characterization,' Turkish Journal of Chemistry, 20:43-53 (1996).

Kister, et al., 'Effects of morphology, conformation and configuration on the IR and Raman spectra of various poly(lactic acid)s,' Polymer, 39(2): 267-273 (1998).

Koelling, et al., 'In vitro real-time aging and characterization of poly(L/D-lactic acid),' Proceedings of the 1997 1fth Southern Biomedical Engineering Conference (Cat. No. 97TH8270), pp. 197-201.

Kontio, et al., 'Fibrous wound repair associated with biodegradable poly-L/D-lactide copolymers implants: study of the expression of tenascin and cellular fibronectin,' Journal of Materials Science-Materials in Medicine, 9:10:603-609 (1988).

Kricheldorf, et al., 'Polyactones: 32. High-molecular weight polylactides by ring-opening polymerization with dibutylmagnesium or butylmagnesium chloride,' Polymer, 36(15):2995-3003 (1995).

L. L. Hench, 'Bioactive materials: The potential for tissue regeneration,' J. Biomed. Materials Research, 41(4):511-518 (1998).

Losken, et al., 'Memory of DL-polylactic acid biodegradable plates,' Ann. Plast. Surg., 32(6):606-611 (1994).

MacDonald, et al., 'Enzymatic degradability of poly(lactide): Effects of chain stereochemistry and material crystallinity,' Macromolecules, 29(23):7356-7361 (1996).

Mainil-Varlet, et al., 'Effect of in vivo and in vitro degradation on molecular and mechanical properties of various low-molecular weight polylactides,' Journal of Biomedical Materials Research, 36(3):360-380 (1997).

Matsumura, et al., 'Novel ring opening polymerization of lactide by lipase,' Macromol. Symp., 130:285-304 (1998).

Mauduit, J. et al.; "Hydrolytic degradation of films prepared from blends of high and low molecular weight poly (DL lactic acid)s" Journal of Biomedical Materials Research, 1996, vol. 30, p. 201-207.

(56) References Cited

OTHER PUBLICATIONS

Morita, et al., 'Intravitreous delivery of dexamethasone sodium m-sulfobenzoate from poly(DL-lactic acid) implants,' Biological & Pharmaceutical Bulletin, 21 (2): 188-190 (1998).
Okihara, et al., Crystal structure of stereocomplex of poly(L-lactide) and poly(D-lactide), Journal of Macromolecular Science-Physics, B30(1 and 2): 119-140 (1991).
Okuzaki, et al., Mechanical Properties and Structure of the Zone-Drawn Poly(l-lactic acid) Fibers, Journal of Polymer Science, Part B, Polymer Physics, 37:991-996 (1999).
Oriented Polymer Materials, Edited by Stoyko Fakirov, published by Huthig & Wepf Verlag Zug, Heidelberg, Oxford CTIUSA, Table of Contents pp. v, viii, ix-xix (1996).
Penning, et al., 'Preparation and properties of absorbable fibres from I-lactide copolymers,' Polymer, 34(5):942-951 (1993).
Pitt, et al., 'Modification of the rates of chain cleavage of polY(e-caprolactone) and related polyesters in the solid state,' Journal of Controlled Release, 4:283-292 (1987).
Pitta, et al., "Comparison of fixation of the femoral component without cement and fixation with use of a bone-vacuum cementing technique for the prevention of fat embolism during total hip arthroplasty," J. Bone Joint Surg., 81-A(6)-831-843 (1999).
Rak, et al., 'The preparation and characterization of poly(D,L-lactic acid) for use as a biodegradable drug carrier,' (1985) liverpool Poly tech., liverpool, UK, Pharmaceutica Acta Helvetiae, 60:(5-6):162-169.
Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).
Schliephake, et al., 'Reconstruction of the mandible by prefabricated autogenous bone grafts,' Int. J. Oral Maxillofac. Surg., 26:244-252 (1997).
Stahelin, et al., Clinical degradation and biocompatibility of different bioabsorbable interference screws: a report of six cases: Arthroscopy: The Journal of Arthroscopic & Related Surgery, 13(2):238-244 (1997).
Steendam, et al., The role of elastic relaxation in drug delivery from poly(DL-lactic acid) based tablets. A shape memory phenomenon: Proceedings of the International Symposium on Controlled Release of Bioactive Materials, 25:128-129 (1998).
Stevels, et al., 'Blends van blok copolymeren die een poly(L-lactide) of poly(D-lactide) blok bevatten,' Biomedical Science and Engineering Meeting, pp. 107-110 (1994).
Structure and Properties of Oriented Polymers, Ed. I. M. Ward, Department of Physics, UniverSity of Leads, England, a Halsted Press Book, John Wiley & Sons, New York-Toronto (1975) Table of Contents.
Tagl, "Thesis—The morselized and impacted bone graft animal experiments on proteins, impaction and load," Acta Orthop. Scand. Suppl., 290:1-40 (2000).
Temenoff et al., "Injectable biodegradable materials for orthopedic tissue engineering," Biomaterials, 21 :2405-2412 (2002).
Tschakaloff, et al., 'Degradation kinetics of biodegradable DL-polyactic acid biodegradable implants depending on the site of implantation,' International Journal of Oral and Maxillofacial Surgery, 23(6 Pt2 ):443-445 (1994).
Tsuji, et al., Stereocomplex formation between enantiomeric poly(lactic acid). VIII. Complex fibers spun from mixed solution of poly(D-lactic acid) and poly(L-lactic acid), Journal of Applied Polymer Science, 51(2):337-344 (1994).
Chart BMEN 343 Polymer Tg Chart.
Examination Report for counterpart Australian Application No. 2008242737 dated Aug. 10, 2012, 3 pages.
First Office Action for Japanese Application No. 2010-503579 dated Mar. 6, 2012, 6 pages.
International Preliminary Report on Patentability and Written Opinion for PCT Application No. PCT/GB2008/001331 dated Oct. 20, 2009, 8 pages.
International Search Report and Written Opinion for PCT/GB2008/001331 dated Aug. 25, 2008.
Office Action for Australian Patent Application No. 2008240418 dated Dec. 2, 2011.
Office Action for Japanese Application No. 2010504268 dated Jan. 8, 2013, 4 pages.
Office Action for Japanese Application No. 2010504268 dated Jul. 17, 2012, 6 pages.
Second Office Action for Japanese Application No. 2010-503579 dated Feb. 19, 2013, 3 pages.
Summary of Office Action, dated Mar. 19, 2012, 1 page.
Water Transport in Polylactic Acid (PLA), Siparsky et al. Journal of Environmental Polymer Degradation, vol. 5, No. 3, 1997.
International Preliminary Report on Patentability and Written Opinion for PCT/GB2012/052478 dated Apr. 8, 2014, 14 pages.
International Search Report for PCT Application No. PCT/GB2012/052478, dated Jun. 20, 2013, 6 pages.
International Preliminary Report on Patentability and Written Opinion for PCT/GB2012/052470 dated Apr. 8, 2014, 6 pages.
International Search Report for PCT Application No. PCT/GB2012/052470 dated Feb. 22, 2013, 2 pages.
International Search Report for PCT Application No. PCT/GB2012/052475 dated Mar. 8, 2013, 3 pages.
International Preliminary Report on Patentability and Written Opinion for PCT Application No. PCT/GB2012/052475 dated Apr. 8, 2014, 10 pages.
International Preliminary Report on Patentability and Written Opinion for PCT Application No. PCT/GB2012/052480 dated Apr. 8, 2014, 12 pages.
International Search Report for PCT Application No. PCT/GB2012/052480 dated May 31, 2013, 4 pages.
Decision of Rejection for Japanese Patent Application No. 2010-504201 dated Jun. 2, 2014, 6 pages.
Song, K. et al. "Double bubble tubular film extrusion of polybutylene terephthalate—polyethylene terephthalate blends." Publication of Society of Plastic Engineers, Dec. 1999.
Atkins, G.J. et al. "Role of polyethylene particles in peri-prosthetic osteolysis: A Review." World of Journals of Orthopedics, 2(10), Oct. 18, 2011, pp. 93-101.
Hill, R.G., "Chapter 10: Biomedical Polymers." Biomaterials, artificial organs and tissue engineering. Imperial College London, UK (2005), 7 pages.
Vert, M. et al. "Bioresorbability and biocompatibility of aliphatic polyesters", Journal of Materials Science: Materials in Medicine 3, 1992, pp. 432-446.

* cited by examiner

GRAFT FIXATION

CROSS-REFERENCE TO RELATED APPLICATIONS

This application is a U.S. National Stage Application, submitted under 35 U.S.C. 371, claiming priority to PCT International Patent Application PCT/US2008/060401 filed on Apr. 16, 2008, which claims priority to U.S. Patent Application No. 60/912,828 filed on Apr. 19, 2007, the disclosures of which are incorporated herein by reference in their entirety.

BACKGROUND

1. Field of the Invention

The present disclosure relates generally to tissue graft fixation and, more particularly, to tissue graft fixation via the use of shape memory polymer material.

2. Related Art

A ligament, such as an anterior cruciate ligament (ACL), that has ruptured and is non-repairable, is generally replaced arthroscopically by a tissue graft. The tissue graft may be harvested from a portion of a patellar tendon having so called "bone blocks" at each end, and from the semitendonosis and gracilis. Alternatively, the tissue graft can be funned from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures arc used to affix each end of the tissue graft to a fastener (e.g., an interference screw or a post), which is then secured to the bone. The use of a fastener, such as an interference screw, may create complications for several reasons: the possibility of the screw threads damaging the grafts during screw installation if the screw is too big in relation to the graft and/or if the space between the passage and the grafts is too small, the graft rotating with the screw during screw installation so that the optimal position of the grafts is lost and/or the grafts are damaged, divergence of the grafts and/or screw occurring, the requirement of a range of fastener sizes for different patients, and, if the screw is non-metal, the possibility of the screw breaking during insertion.

SUMMARY

In one aspect, the present disclosure relates to an anchor for fixating a tissue graft to bone. The anchor includes a through hole extending an entire length of the anchor. The anchor includes a polymer composition including shape memory qualities. In an embodiment, the through hole is circular, star-shaped, or rectangular. In another embodiment, the anchor further includes a component disposed within the through hole of the anchor, wherein the component includes a polymer composition having shape memory qualities. In yet another embodiment, the through hole is divided into two sections. In a further embodiment, the through hole is divided into four sections.

In another aspect, the present disclosure relates to an anchor for fixating a tissue graft to bone. The anchor includes a first groove extending an entire length of the anchor and a second groove extending an. entire length of the anchor. The anchor includes a polymer composition. having shape memory qualities. In an embodiment, the first groove and the second groove both include barbs.

In yet another aspect, the present disclosure relates to an anchor for fixating a tissue graft to bone. The anchor includes a cross-section in a shape of a cross and a polymer composition including shape memory qualities.

In a further embodiment, the present disclosure relates to an anchor for fixating a tissue graft to bone. The anchor includes a body having a curved top portion, a curved bottom portion, and two sides located between the top portion and the bottom portion. In an embodiment, the sides are curved inward toward the body of the anchor.

In yet a further embodiment, the present disclosure relates to a method of fixating a tissue graft to bone. The method includes providing an anchor having a through hole extending an entire length of the anchor. The anchor includes a polymer composition having shape memory qualities; inserting an end of a tissue graft into the through hole; inserting the anchor into a bone tunnel; providing the anchor with energy to deform the anchor and fixate the graft within the bone tunnel.

In an embodiment, the method further includes a component disposed within the through hole, the component including a polymer composition having shape memory qualities. In another embodiment, the through hole is divided into two sections, wherein the method further includes inserting ends of a tissue graft into the sections. In yet another embodiment, the through hole is divided into the four sections, wherein the method further includes inserting ends of multiple tissue grafts into the sections.

In an embodiment, the present disclosure relates to a method of fixating tissue grafts to bone. The method includes providing at least two tissue grafts; coupling the at least two tissue grafts; inserting the at least two tissue grafts into a bone tunnel; inserting an anchor into the bone tunnel such that the anchor is located between the at least two tissue grafts; and providing energy to the anchor to deform the anchor and fixate the at least two tissue grafts within the bone tunnel.

Further features, aspects, and advantages of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings:

FIGS. 6A and 6B show cross-sectional views of an anchor of an eighth embodiment of the present disclosure before and after deformation of the anchor.

DETAILED DESCRIPTION OF THE EMBODIMENTS

Figure 1A:
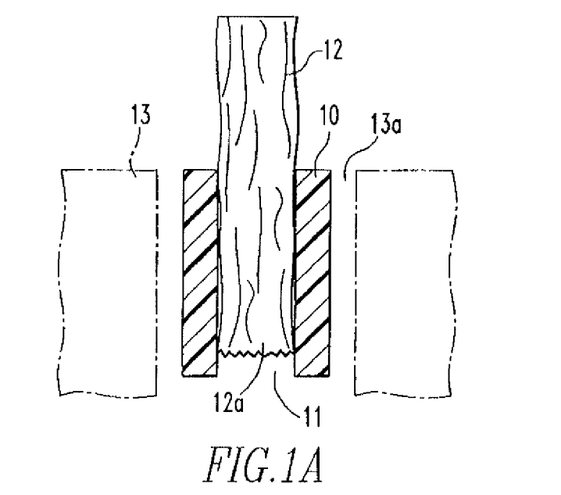
FIGS. 1A and 1B show a cross-sectional view of an end of a tissue graft disposed within an anchor of a first embodiment of the present disclosure both before and after deformation of the anchor.
Figure 1B:
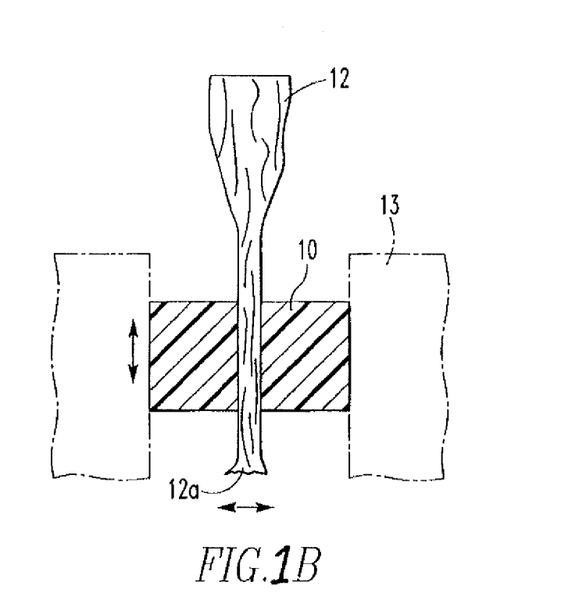

FIGS. 1A and 1B show cross-sectional views of a cylindrical anchor 10 with a central through hole 11 into which an end 12a of a tissue graft 12 is placed. The anchor 10 is then loosely press fit into a pre-formed passage 13a in bone 13, such as a femoral passage in a femur, as described above. Upon providing the anchor 10 with energy, the anchor 10 expands radially and shrinks axially, as shown by arrows in FIG. 1B, thereby fixating the tissue graft 12 and anchor 10 to the bone 13.

Figure 2A:
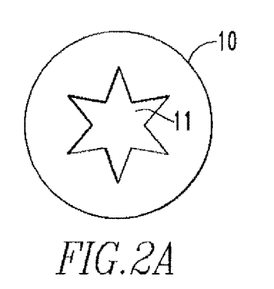
FIGS. 2A and 2B show cross-sectional views of an anchor of a second embodiment of the present disclosure before and after deformation of the anchor.
Figure 2B:
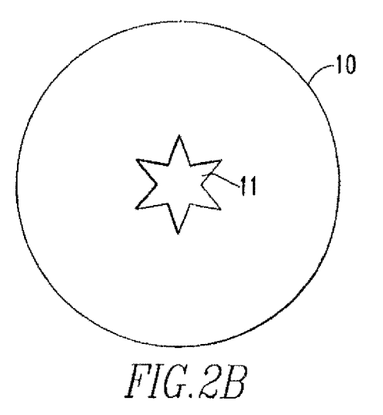
Figure 2C:
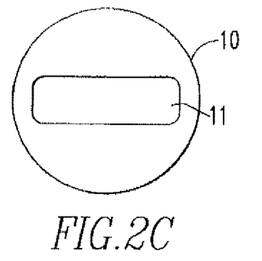
FIGS. 2C and 2D show cross-sectional views of an anchor of a third embodiment of the present disclosure before and after deformation of the anchor.
Figure 2D:
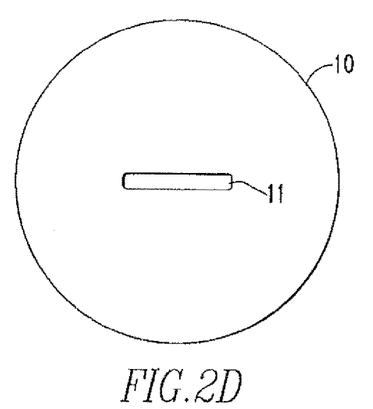
Figure 2E:
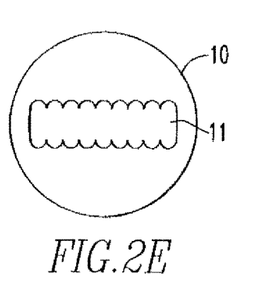
FIGS. 2E and 2F show cross-sectional views of an anchor of a fourth embodiment of the present disclosure before and after deformation of the anchor.
Figure 2F:
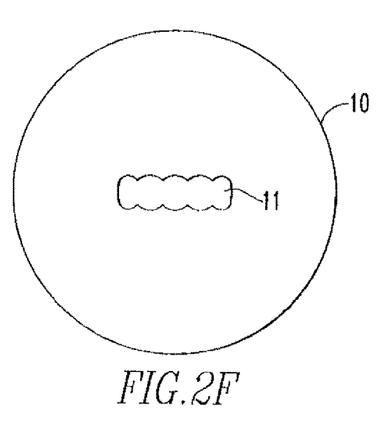

Alternative embodiments of the anchor 10 include those shown in FIGS. 2A, 2C, and 2E, which are similar to the anchor described above except that the through holes 11 include those shaped as a star (FIG. 2A), a slot (FIG. 2C), and a toothed slot (FIG. 2E). FIGS. 2B, 2D, and 2F show the anchors 10 of FIGS. 2A, 2C, and 2E, respectively, after the anchors 10 are provided with energy. Other shapes for the through holes 11 are also within the scope of this disclosure. It is believed that having a through hole with the shapes shown in FIGS. 2A, 2C, and 2E would increase the fixation of the graft to the anchor due to an increase in the amount of surface area and points of contact engaging the graft. The number of holes 11 in the anchor 10 may vary.

The anchor comprises polymeric shape memory material. Shape memory polymers, which can be resorbable or non-resorbable, are known in the art and any biocompatible polymeric shape memory material can be used in the context of the present disclosure. Specific polymers that may be used include polyetheretherketone (PEEK), polymethyl methacrylate (PMMA), polyethyl methacrylate (PTMA), polyacrylate, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof.

The anchor 10 may be formed by a process that would provide the anchor 10 with shape memory properties, such as, without limitation, zone drawing, hydrostatic extrusion, die drawing, compression flow molding, thermoforming, rolling, and roll drawing. The through hole 11 may be formed in the anchor 10 while it is being manufactured. Alternatively, the through hole 11 may be formed in the anchor 10 post processing by drilling or by any other method of forming the through hole 11.

Generally, polymers that display shape memory qualities show a large change in modulus of elasticity at the glass transition temperature ($T_g$). The shape-memory function can be achieved by taking advantage of this characteristic. Namely, a molded article (primary molded article) to which a definite shape (the original shape) has been imparted by a common method for molding plastics, is softened by providing the article with energy and heating to a temperature ($T_f$) higher than the $T_g$ of the polymer, but lower than the melting temperature ($T_m$) thereof so as to deform it into a different shape. Next, the molded article is cooled to a temperature lower than the $T_g$, while maintaining the thus deformed shape (secondary molded article). When it is heated again to a temperature higher than the secondary molding temperature $T_f$, but lower than the $T_m$, the shape of the secondary molded article disappears and thus the article is recovered to the original shape of the primary molded article.

For the purposes of this disclosure, a molded article (i.e. the above-mentioned anchor), having a definite shape (original shape) is formed from polymer material and is provided with energy to heat the article to a temperature above the glass transition temperature of the polymer, but lower than the melting temperature ($T_m$ thereof so as to deform it into a different shape and effectively wedge the article between the tissue graft and the bone. In this manner, the tissue graft becomes fixed to the bone. However, for the purposes of this disclosure, rather than cooling the anchor and heating it again until it recovers its original shape, the anchor is kept in this deformed shape so as to maintain fixation of the tissue graft to the bone. The glass transition temperature of the polymer material will vary based on a variety of factors, such as molecular weight, composition, structure of the polymer, and other factors known to one of ordinary skill in the art.

Examples of adding energy to the polymer material include electrical and thermal energy sources, the use of force, or mechanical energy, and/or a solvent. Examples of thermal energy sources include a heated liquid, such as water or saline. It is also within the scope of this disclosure that once the anchor 10 is placed in the bone, body heat would be transferred from blood and tissue, via thermal conduction, to provide the energy necessary to deform the shape memory polymer material. In this instance, body temperature would be used as the thermal energy source. Examples of electrical energy sources include heat generating devices such as a cauterizing device or insulated conductor, as more fully described in PCT Application No. PCT/US2008/056828, the disclosure of which is incorporated herein by reference in its entirety, or a heating probe, as more fully described in PCT Application No. PCT/US2008/056836, the disclosure of which is incorporated herein by reference in its entirety. For instance, the anchor 10 may include a hole in the body of the anchor 10 that a heating device, such as the heating probe described above, may be inserted into.

Any suitable force that can be applied either preoperatively or intra-operatively can be used as a form of energy. One example includes the use of ultra sonic devices, which can relax the polymer material with minimal heat generation. Solvents that could be used as the form of energy include organic-based solvents and aqueous-based solvents, including body fluids. Care should he taken that the selected solvent is not contra indicated for the patient, particularly when the solvent is used intra-operatively. The choice of solvents will also be selected based upon the material to be relaxed. Examples of solvents that can be used to relax the polymer material include alcohols, glycols, glycol ethers, oils, fatty acids, acetates, acetylenes, ketones, aromatic hydrocarbon solvents, and chlorinated solvents.

Figure 3A:
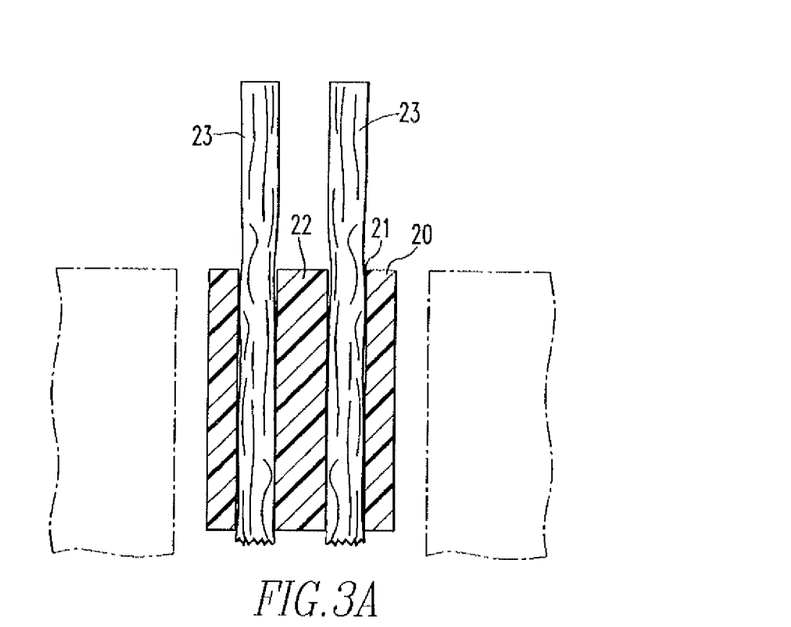
FIGS. 3A and 3B show cross-sectional views of an end of a tissue graft disposed within an anchor of a fifth embodiment of the present disclosure before and after deformation of the anchor.
Figure 3B:
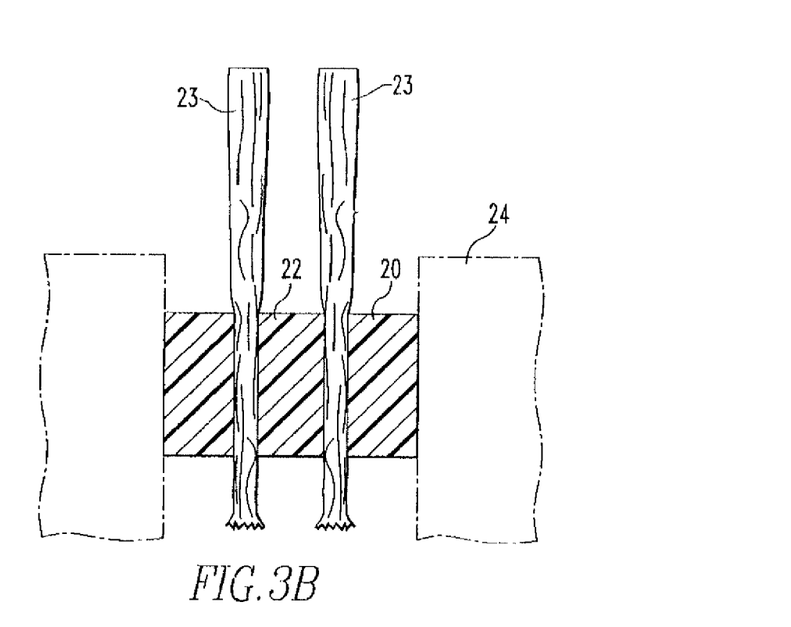

A further embodiment of the anchor is shown in FIGS. 3A and 3B. The anchor 20 includes a through hole 21 and a component 22 disposed within the through hole 21. Multiple grafts 23 can be placed into the through hole 21 along with the component 22, which, as shown in FIG. 3B, decreases in length and increases in diameter, similar to anchor 20, thereby providing further fixation of the grafts 23 to anchor 20 and therefore the bone 24. The anchor 20 and component 22 may be formed by a process that would provide the anchor 20 and component 22 with shape memory properties, such as, without limitation, zone drawing, hydrostatic extrusion, die drawing, compression flow molding, thermoforming, rolling, and roll drawing. The through hole 21 may be formed in the anchor 20 while it is being manufactured. Alternatively, the through hole 21 may be formed in the anchor 20 post processing by drilling or by any other method of forming the through hole 21.

Figure 4A:
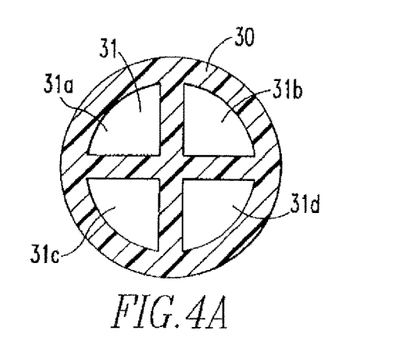
FIGS. 4A and 4B show cross-sectional views of an anchor of a sixth embodiment of the present disclosure before and after deformation of the anchor.
Figure 4B:
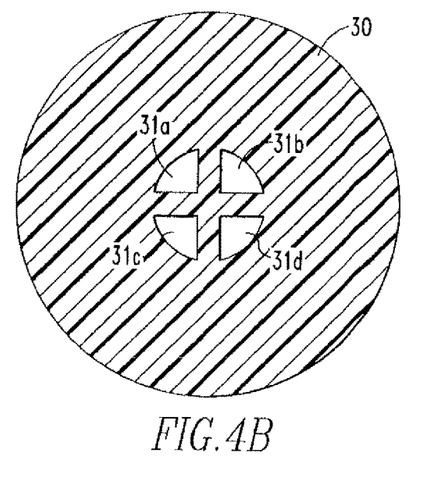
Figure 5A:
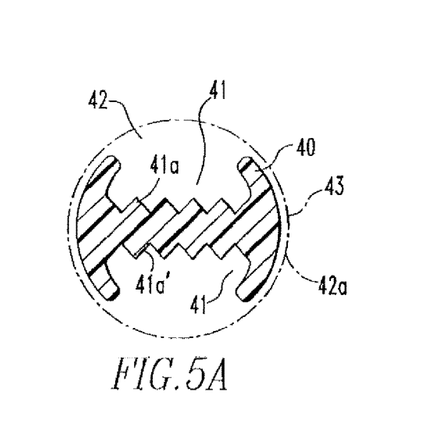
FIGS. 5A and 5B show cross-sectional views of an anchor of a seventh embodiment of the present disclosure before and after deformation of the anchor.
Figure 5B:
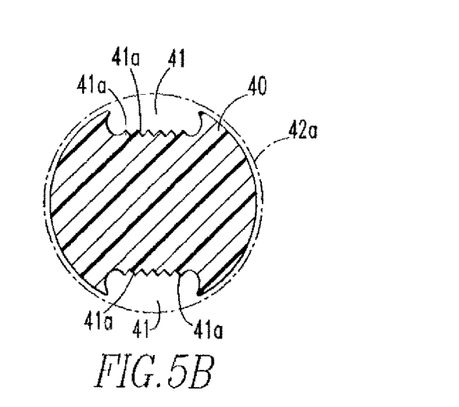
Figure 6A:
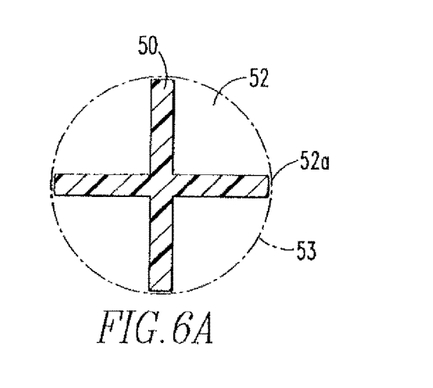

Another embodiment is shown in FIGS. 4A-4B, 5A-5B, and 6A-6B. The anchor 30 of FIG. 4A includes a through hole 31 that is divided into four separate openings 31a-31d allowing the possibility of up to four tissue graft ends being fixated to the anchor 30 when the anchor 30 is provided with energy, as shown in FIG. 4B. FIGS. 5A-5B show an. anchor 40 having two grooves 41, both of which may extend the entire length of the anchor 40 or a partial length. Surfaces 41a of the grooves 41 include features, such as barbs 41a', which may allow further fixation of the anchor 40 to the graft upon providing the anchor 40 with energy, as shown in FIG. 5B. FIGS. 6A-6B show an anchor 50 in the shape of a cross. Similar to the anchor 30 of FIGS. 4A-4B, anchor 50 allows for the possibility of four tissue graft ends being fixated to the anchor 50 when the anchor 50 is provided with energy, as shown in FIG. 6B.

The anchors 40,50 of FIGS. 5A and 6A expand to cause an interference fit against walls 42a,52a of the bone tunnels 42,52, thereby not only fixating the anchors 40,50 to the walls 42a,52a, but also fixating tissue graft ends to the bone 43,53, which allow direct osseointegration of the graft to the walls 42a,52a. The anchors 30, 40, 50 may be formed by a process that would provide the anchors 30, 40, 50 with shape memory properties, such as, without limitation, zone drawing, hydrostatic extrusion, die drawing, compression flow molding, thermoforming, rolling, and roll drawing. The through hole 31, openings 31a-31d, grooves 41, and barbs 41a' may be formed in the anchors 30, 40 while it is being manufactured. Alternatively, these features may be formed in the anchors 30,40 post processing by drilling or by any other method.

Figure 7A:
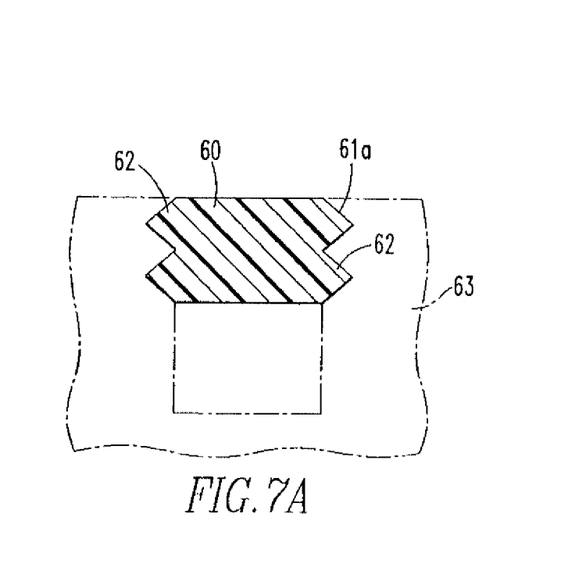
FIGS. 7A and 7B show cross-sectional views of a bone tunnel having surface features on walls of the tunnel.
Figure 7B:
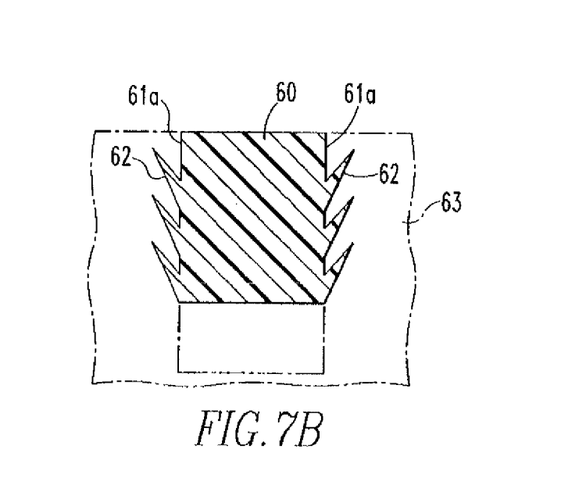

As shown in FIGS. 7A and 7B, the walls 61a may include surface features 62, such as barbs and/or spikes, which would allow more integration of the anchor 60 into the bone 63 upon providing the anchor 60 with energy, thereby increasing fixation of the anchor 60, and therefore a graft, to the bone 63. The surface features 62 may be made via the use of a mechanical tool or other devices known to one of skill in the art for making the features 62.

Figure 8A:
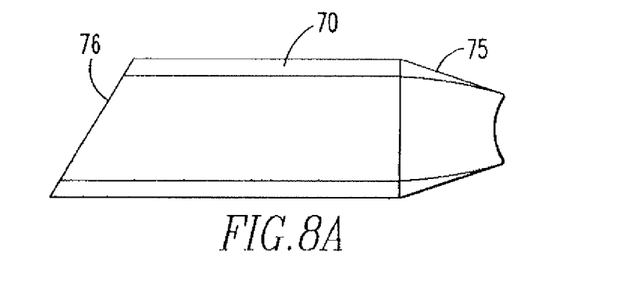
FIG. 8A shows a side view of an anchor of a ninth embodiment of the present disclosure
Figure 8B:
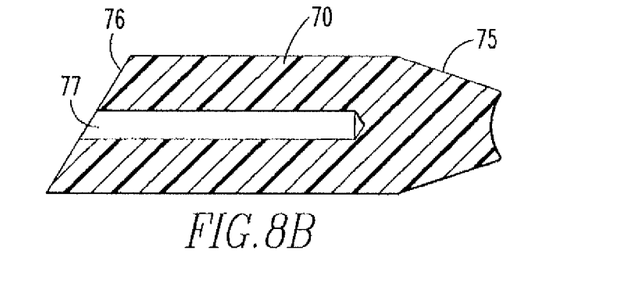
FIG. 8B shows a cross-sectional view of the anchor of FIG. 8A.
Figure 8C:
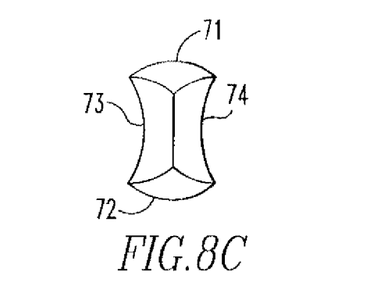
FIG. 8C shows a front view of the anchor of FIG. 8A.

In an embodiment shown in FIGS. 8A-8C, an anchor 70 has been shaped to aid insertion into a bone tunnel containing ligaments or bone block, as will be further described below. The anchor 70 includes substantially rounded top and bottom portions 71,72 and two sides 73,74, located between the top and bottom portions 71,72, both of which are configured to house graft ends when the plug is disposed within a hone tunnel, as will be further described below. The anchor 70 also includes a tapered front portion 75, an angled back portion 76, and an opening 77 that partially extends a length of the anchor 70. The opening 77 is configured for engagement with a delivery device for delivery of the anchor 70 into a bone tunnel, as will be further described below.

Figure 9:
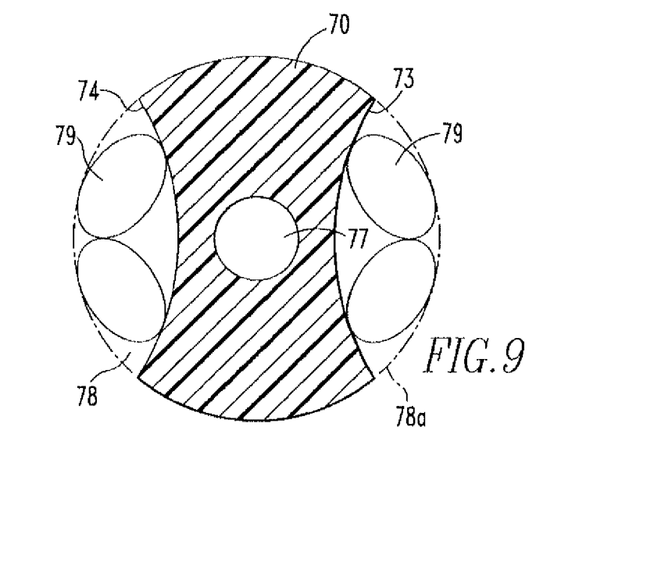
FIG. 9 shows a cross-sectional view of the anchor of FIG. 8A in a bone tunnel and after deformation of the anchor.

In use, as shown in FIG. 9, the anchor 70 is inserted into a bone tunnel 78, via the use of a delivery device, as mentioned above, such that the graft ends 79 extend along the sides 73,74 of the anchor 70. The anchor 70 is then provided with energy, via the use of one of the heating devices described above, by inserting the heating device into the opening 77 and activating it, thereby resulting in the anchor 70 expanding to compress the graft ends 79 against the bone tunnel wall 78a and fixate the plug 70 and the graft ends 79 within the bone tunnel 78. Other energy sources may also be used. The anchor 70 may be of various sizes to accommodate the size of the bone tunnel 78 and substantially increase the possibility of engagement of the anchor 70 and the graft ends 79 with the wall 78a upon deformation of the anchor 70.

The anchor 70 may be formed by a process that would provide the anchor 70 with shape memory properties, such as, without limitation, zone drawing, hydrostatic extrusion, die drawing, compression flow molding, thermoforming, rolling, and roll drawing. Alternatively, the anchor 70 is processed via one of the methods described above and subsequently machined to include the shape of the sides 73,74 and the top and bottom portions 71,72. The opening 77 may be formed in the anchor 70 while it is being manufactured. Alternatively, the opening 71 may be formed in the anchor 70 post processing by drilling or by any other method of forming the opening 71.

EXAMPLE

An 8.5 mm hole was drilled through the centre of a block of 20 pcf sawbone having the following dimensions: 42 mm long, 31 mm wide, and 31 mm thick.

Two pieces of 7 inch long 125 lb braided nylon rope were doubled over and inserted into the hole so that the four ends of rope passed all the way through the hole in the sawbone. An anchor including Poly (D,L lactide-co-glycolide) and calcium carbonate was inserted into the hole ensuring that the strands of nylon rope passing through the hole did not cross over one another and each of the four ends of nylon had its own quadrant of the hole. The anchor was processed via a die drawing process to include shape memory qualities. The ratio of lactide:glyeolidc was 85:15 and the calcium carbonate was present at between about 35.5% by weight of the polymer composition. Once in place, the plug was relaxed by immersion of the block, plug, and rope into hot water (approximately 80° C. for 5 min). When the block containing the plug and rope had cooled to room temperature, it was inserted into an aluminum sleeve having similar dimensions to the sawbone block.

Figure 10:
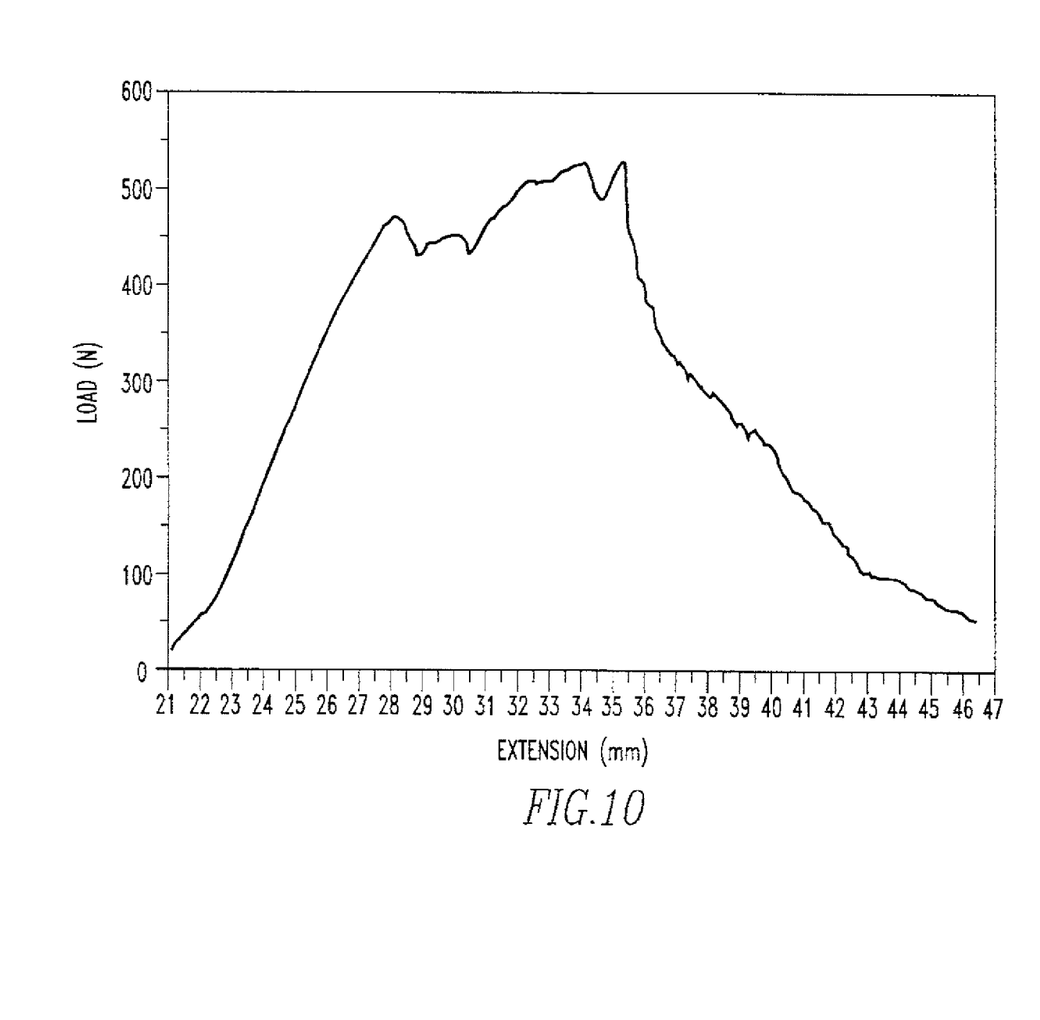
FIG. 10 shows mechanical testing data for the anchor of the present disclosure.

Mechanical testing was carried out using an Instron 5566 with a 10 kN load cell. The aluminum sleeve housing the sawbone block was clamped in a first grip of the Instron and the nylon loops were clamped in a second grip, specifically, the loops were clamped to the crosshead of the Instron. The crosshead was extended until the loops were taut, which, as shown in FIG. 10, occurred when the crosshead was extended 21 mm, and then testing began. Testing was carried out with a crosshead speed of 25 mm/min and a pre-load of 22.3N. As shown in FIG. 10, the plug was found to have a maximum fixation strength of 532 N.

Figure 11A:
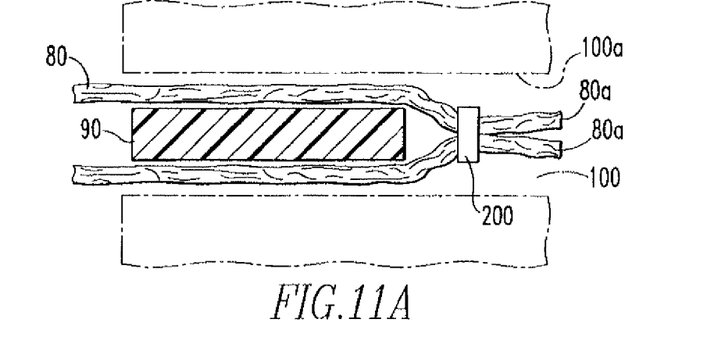
FIGS. 11A and 11B show a method of fixating tissue grafts within a bone tunnel using an anchor of the present disclosure.
Figure 11B:
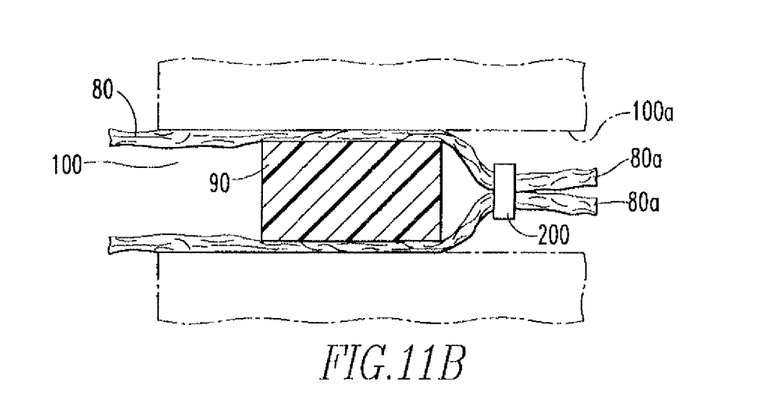

A further embodiment is shown in FIGS. 11A and 11B. In order to substantially reduce the graft ends 80a from slipping between an anchor 90 and the bone tunnel wall 100a, the ends 80a may be coupled at one point via a biocompatible connector 200 including, without limitation, a suture, a clip, or staple. The grails 80 arc placed into a previously drilled hone tunnel 100 and an anchor 90 is then inserted between the grafts 80 and deformed by providing the anchor 90 with energy, as shown in FIG. 11B, to fixate the grafts 80 within the tunnel 100.

The anchor 90 may be formed by a process that would provide the anchor 90 with shape memory properties, such as, without limitation, zone drawing, hydrostatic extrusion, die drawing, compression flow molding, thermoforming, rolling, and roll drawing.

The anchors described above may include a reinforced polymeric material. Preferably, the reinforced polymeric material comprises a composite or matrix including reinforcing material or phases such as fibers, rods, platelets, and fillers. More preferably, the polymeric material can include glass fibers, carbon fibers, polymeric fibers, ceramic fibers, or ceramic particulates. Other reinforcing material or phases known to one of ordinary skill in the art could also be used. One or more material from which the anchor is formed may be porous. Porosity can allow infiltration by cells from surrounding tissues, enhancing integration of the device by processes such as osseointegration.

In addition, one or more actives/agents may be incorporated into the material of the anchor. Suitable actives/agents include bone morphogenic proteins, antibiotics, anti-inflammatories, angiogenic factors, osteogenic factors, monobutyrin, thrombin, modified proteins, platelet rich plasma/solution, platelet poor plasma/solution, bone marrow aspirate, and any cells sourced from flora or fauna, such as living cells, preserved cells, dormant cells, and dead cells. It will be appreciated that other bioactive agents known to one of ordinary skill in the art may also be used. Preferably, the active agent is incorporated into the polymeric shape memory material, to be released during the relaxation or degradation of the polymer material. Advantageously, the incorporation of an active agent can act to combat infection at the site of implantation and/or to promote new tissue growth.

The anchor described above may also include at least one feature, such as protrusions, that arc coupled to a surface of the anchor via a variety of methods, such as an interference fit between the polymer and the protrusions, adhesion of the protrusion to the polymer, or any other method known to one of ordinary skill in the art. In addition, the number of protrusions present on the surface of the anchor may vary. The protrusions may provide multiple contact points to increase the friction between the anchor and the bone, thereby providing increased fixation between the tissue graft and the bone. The protrusions may be selected from a group that includes a metal material, a non-metal material, a polymer material, and combinations thereof and may be of any shape or size. If a polymer material is used for the protrusions, the polymer material may include a resorbable or non-resorbable polymer material.

Use of the protrusions may he eliminated by including a particulate material within or on an outer surface of the anchor. The particulate material may include a ceramic material, a crystalline polymer, or any other type of material that would provide the polymer material with multiple contact points to increase the friction between the polymer material and the bone.

The anchors described above, and especially anchors 10,20, may he biaxially oriented to have an internal diameter that decreases and an external diameter that increases when the anchor is provided with energy. This allows for the internal diameter to further grip the anchor to the tissue graft(s) and the outer diameter to engage the surrounding bone, thereby locking the tissue graft(s) in place. In order to make an anchor of biaxially oriented shape memory polymer material, a rod of shape memory polymer material may be die drawn over a mandrel. Further discussion of this process can he found in U.S. Patent Application Ser. No. 60/912,740, the disclosure of which is incorporated herein by reference in its entirety.

The shape memory anchors of the present disclosure may substantially reduce the need to thrcad/pre-tap the bone tunnel before insertion of the anchor into the bone tunnel, especially when a patellar tendon is used as the tissue graft. In addition, it is believed that the anchor would offer improved fixation over existing systems. Furthermore, the anchors may substantially reduce the possibility of making a range of fasteners to fit the patient, thereby possibly offering a 'one size fits all' approach.

In view of the foregoing, it will be seen that the several advantages of the invention are achieved and attained.

The embodiments were chosen and described in order to best explain the principles of the disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An anchor for fixating a tissue graft to bone, the anchor comprising:
    an elongated body disposable into a bone tunnel in a bone and made from a shape-memory material, the elongated body comprising:
    a non-tapered proximal portion, comprising:
        a first concave outer surface extending longitudinally along the entire non-tapered proximal portion to define a first longitudinal channel along a first side of the elongated body wherein the first concave outer surface has a shape memory configured to compress a first tissue graft end portion against the bone tunnel wall in response to receiving a shape memory activation energy;
        a first convex outer surface extending longitudinally along an entire second side of the non-tapered portion and configured to engage a bone tunnel wall of the bone when the elongated body is inserted into the bone tunnel; and
    a tapered distal portion extending longitudinally from the non-tapered proximal portion wherein the-first concave outer surface extends longitudinally along the entire tapered distal portion.

2. The anchor of 1, further comprising a cavity extending longitudinally into the elongated body from a proximal end of the elongated body, the cavity shaped to receive a delivery device and/or a heating device.

3. The anchor of claim 2, wherein the non-tapered proximal portion further comprises:
- a second concave outer surface extending longitudinally along the entire non-tapered proximal portion to define a second longitudinal channel along a third side of the elongated body opposite the first side of the elongated body wherein the second concave outer surface has a shape memory configured to compress a second tissue graft end portion against the bone tunnel wall in response to receiving the shape memory activation energy; and
- a second convex outer surface extending longitudinally along an entire fourth side of the non-tapered portion opposite the second side of the non-tapered portion and configured to engage the bone tunnel wall of the bone when the elongated body is inserted into the bone tunnel.

4. The anchor of claim 3, wherein the second concave outer surface extends longitudinally along the entire tapered distal portion.

* * * * *